US010683550B2

(12) United States Patent
Cai et al.

(10) Patent No.: US 10,683,550 B2
(45) Date of Patent: Jun. 16, 2020

(54) HNF4G-RSPO2 FUSION GENE AND USE THEREOF IN TREATMENT OF CANCER

(71) Applicant: CROWN BIOSCIENCE, INC. (TAICANG), Taicang (CN)

(72) Inventors: Jie Cai, Taicang (CN); Henry Li, Taicang (CN)

(73) Assignee: CROWN BIOSCIENCE, INC. (TAICANG), Taicang, Jiangsu (CN)

( * ) Notice: Subject to any disclaimer, the term of this patent is extended or adjusted under 35 U.S.C. 154(b) by 453 days.

(21) Appl. No.: 15/301,381

(22) PCT Filed: Apr. 3, 2015

(86) PCT No.: PCT/CN2015/075882
§ 371 (c)(1),
(2) Date: Apr. 3, 2018

(87) PCT Pub. No.: WO2015/149720
PCT Pub. Date: Oct. 8, 2015

(65) Prior Publication Data
US 2018/0282814 A1    Oct. 4, 2018

(30) Foreign Application Priority Data

Apr. 4, 2014   (CN) .......................... 2014 1 0135569

(51) Int. Cl.
C12Q 1/64       (2006.01)
C12P 19/34      (2006.01)
C12Q 1/6886     (2018.01)

(52) U.S. Cl.
CPC ..... *C12Q 1/6886* (2013.01); *C12Q 2600/106* (2013.01); *C12Q 2600/156* (2013.01)

(58) Field of Classification Search
CPC ............ C12Q 1/6886; C12Q 2600/156; C12Q 1/6883; C12Q 2600/112
See application file for complete search history.

(56) References Cited

U.S. PATENT DOCUMENTS

2001/0053519 A1* 12/2001 Fodor .................. B01J 19/0046
                                                        435/6.11
2011/0077206 A1    3/2011 Xie et al.
2012/0142549 A1    6/2012 Chinnaiyan et al.

FOREIGN PATENT DOCUMENTS

CN   101524529 A   9/2009
CN   102439174 A   5/2012
CN   102459346 A   5/2012
CN   103571848 A   2/2014

OTHER PUBLICATIONS

GenBank Locus NC_000008.11 positions 75407567-75566834 (Jun. 14, 2019) "Hepatocyte nuclear factor 4 gamma", printed from www.ncbi.nlm.nih.gov. pp. 1-54. (Year: 2019).*
GenBank Locus NG_065170 positions 5066-189370 (Jul. 15, 2019) "*Homo sapiens* R-spondin 2 (RSPO2), RefSeqGene on chromosome 8", printed from www.ncbi.nlm.nih.gov. pp. 1-57. (Year: 2019).*
Sonasekar Seshagiri et al: "Recurrent R-spondin fusions in colon cancer", Nature, vol. 488, No. 7413, Jan. 1, 2012 (Jan. 1, 2012), pp. 660-664, XP055060432.
Jamie N. Anastas et al: "WNT signaling pathways as therapeutic targets in cancer", Nature Reviews Cancer, vol. 13, No. 1, Dec. 21, 2012 (Dec. 21, 2012), pp. 11-26, XP055121831.
Flicek et al, Nucleic Acids Research 2014, 42 Database issue: D749-D755.
International Search Report for PCT/CN2015/075882.
Extended European Search Report for EP15772589.6.
Manuel Rieber et al., "p53 inactivation decreases dependence on estrogen/ERK signalling for proliferation but promotes EMT and susceptibility to 3-bromopyruvate in ERa+ breast cancer MCF-7 cells"; Biochemical Pharmacology 88 (2014) 169-177.

* cited by examiner

*Primary Examiner* — Stephen T Kapushoc
(74) *Attorney, Agent, or Firm* — Jun He Law Offices P.C.; James J. Zhu

(57) ABSTRACT

The present disclosure provides methods of detecting a fusion gene of HNF4G and RSPO2 in a nucleic acid-containing sample, and a primer set, a probe set and a kit for detecting the fusion gene are also provided. Animal models for a human disease positive for the fusion gene are also provided herein. In addition, the present disclosure relates to the methods for assessing and identifying an agent effective on the fusion gene of HNF4G and RSPO2 or a human disease positive for a fusion gene of HNF4G and RSPO2 and thereby treating said disease are also provided.

7 Claims, 5 Drawing Sheets

Specification includes a Sequence Listing.

```
GCGGCCCGCGCAGTGATTGCTGCCTTGACCGTCCCTGCTCTTGAAGAGCACCAGCGAAAGCAG
CCAGTCTGAGATATTGACACTACAGAAAAAACTGACAGCTTACTCCTTGTATTGATTCTACTCTTC
TCTACAAATATAGACTCCGTTCCCTACCACAGCCTT|gttcgtggcggagagatgctgatcgcgctgaactgac
cggtgcggcccggggtgagtggcgagtctccctctgagtcctccccagcagcgcggccggcgccggctctttgggcgaac
cctccagttcctagactttgagaggcgtctctccccgcccgaccgcc
```

Figure 2

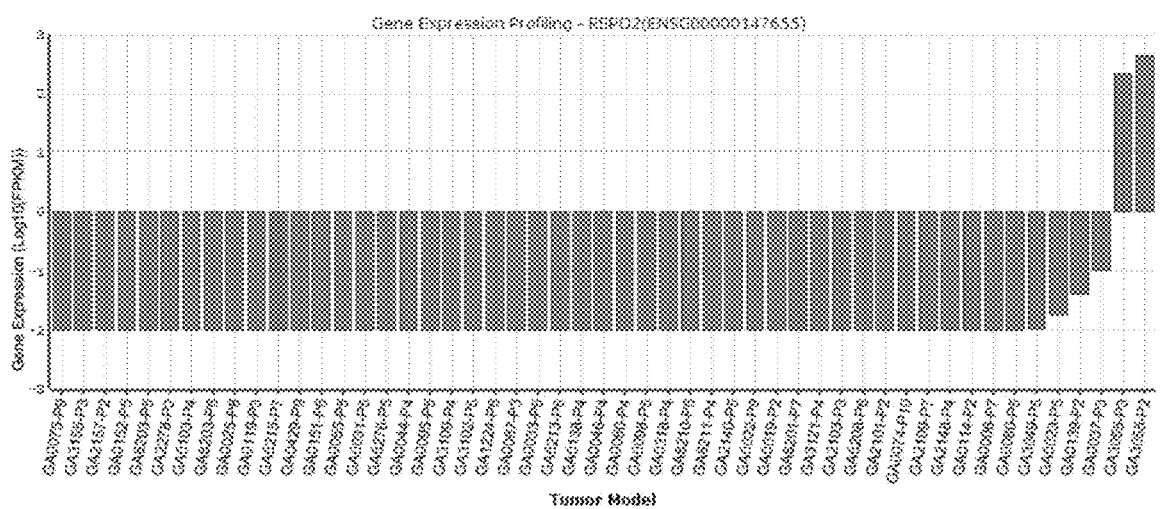

Figure 3

Forward primer
AGCTCCGGGAGCGGCCCGCGCAGGAGCACCAGCGAAAGCAGCCAGTCTGAGATATTG

ACACTACAGAAAAAACTGACAGCTTACTCCTTGTATTGATTCTACTCTTCTCTACAAATATA

GACTCCGTTCCCTACCACAGCCTTgttcgtggcggagagatgctgatcgcgctgaactgaccggtgcggc ccggggtgagtggcgagtctccctctgagtcctccccagcagcgcggccggcgccggctctttgggcgaaccctc Reverse primer
cagttcctagactttgagaggcgtctctccccgcccgaccgcccagatgcagtttcgcctttctcctttgccctca

Figure 4

HNF4G-RSPO2 FUSION GENE AND USE THEREOF IN TREATMENT OF CANCER

CROSS REFERENCE TO RELATED APPLICATIONS

This application is a national phase stage of international application PCT/CN2015/075882, filed Apr. 3, 2015, which relates to and claims priority benefits from CN Patent Application No. 201410135569.9, filed Apr. 4, 2014, the disclosure of which is hereby incorporated by reference by their entirety.

FIELD OF THE INVENTION

The present invention generally relates to a novel fusion gene found in tumor cells, and also treatment targeting such fusion gene.

BACKGROUND OF THE INVENTION

R-spondin protein is an agonist of the classic Wnt/β-catenin signaling pathway. R-spondin gene family members (RSPO) are recently found to be fused with other gene partners in some colorectal cancers (Seshagiri et al, Nature 2012 488(7413): 660-664). It is reported that a EIF3E (exon 1)-RSPO2 (exon 2) fusion gene formed by the fusion of RSPO2 gene and EIF3E gene occurs in 2% of the cancer samples in the patients having colon cancer, while a PTPRK (exon 1)-RSPO3 (exon 2) fusion gene formed by the fusion of RSPO3 gene and PTPRK gene occurs in 8% of the samples. Gene fusion events usually activate expression of R-spondins, which in turn activates Wnt signaling.

Therefore, identification of gene partners for RSPO2 fusion in cancer cell signaling pathway will provide potential opportunities for therapeutic intervention of cancers.

BRIEF SUMMARY OF THE INVENTION

The present invention provides methods of detecting a fusion gene of HNF4G and RSPO2 in a nucleic acid-containing sample, comprising: contacting the sample with a detecting agent which specifically detects a polynucleotide comprising a fusion of a first sequence for HNF4G and a second sequence for RSPO2, and detecting the presence of the polynucleotide.

In some embodiments, the first sequence is a noncoding sequence, and the second sequence is an encoding sequence.

In some embodiments, the methods further comprise detecting the level of the polynucleotide.

In some embodiments, the first sequence for HNF4G is 5' upstream of the second sequence for RSPO2. In some embodiments, the first sequence for HNF4G comprises (a) at least a portion of exon 2 of a HNF4G gene transcript as shown in ENST00000396419, and (b) at least a portion of exon 3 of a HNF4G gene transcript as shown in ENST00000494318.

In some embodiments, the second sequence for RSPO2 comprises: the second sequence for RSPO2 comprises: (a) at least a portion of exon 2 of a RSPO2 gene transcript as shown in ENST00000276659, ENST00000517781, ENST00000522333, or ENST00000378439, or (b) at least a portion of exon 1 of a RSPO2 gene transcript as shown in ENST00000521956.

In some embodiments, the first sequence for HNF4G comprises a sequence selected from a) at least a portion of exon 2 of the HNF4G gene transcript as shown in ENST00000396419, and b) at least a portion of exon 3 of the HNF4G gene transcript as shown in ENST00000494318, and the second sequence for RSPO2 comprises at least a portion of exon 2 of the RSPO2 gene transcript as shown in ENST00000276659, and the exon 2 of the HNF4G gene transcript ENST00000396419 or the exon 3 of the HNF4G gene transcript ENST00000494318 fuses to the exon 2 of the RSPO2 gene transcript.

In some embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000517781, and the exon 2 of the HNF4G gene transcript ENST00000396419 or the exon 3 of the HNF4G gene transcript ENST00000494318 fuses to the exon 2 of the RSPO2 gene transcript.

In some embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000522333, and the exon 2 of the HNF4G gene transcript ENST00000396419 or the exon 3 of the HNF4G gene transcript ENST00000494318 fuses to the exon 2 of the RSPO2 gene transcript.

In some embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000378439, and the exon 2 of the HNF4G gene transcript ENST00000396419 or the exon 3 of the HNF4G gene transcript ENST00000494318 fuses to the exon 2 of the RSPO2 gene transcript.

In some embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 1 of the RSPO2 gene transcript as shown in ENST00000521956, and the exon 2 of the HNF4G gene transcript ENST00000396419 or the exon 3 of the HNF4G gene transcript ENST00000494318 fuses to the exon 1 of the RSPO2 gene transcript.

In some embodiments, the fusion gene comprises a fusion junction of CCACAGCCTT|gttcgtggcg (SEQ ID NO: 3). In some embodiments, the polynucleotide is cDNA or mRNA.

In some embodiments, the detecting agent comprises a first primer directed to the first sequence for HNF4G, and a second primer directed to the second sequence for RSPO2. In some embodiments, the detecting agent comprises a junction primer directed to a fragment containing the fusion junction, and a non-junction primer directed to the first or the second sequence.

In some embodiments, the detecting agent comprises a first probe directed to the first sequence for HNF4G, and a second probe directed to the second sequence for RSPO2. In some embodiments, the detecting agent comprises a junction probe directed to a fragment containing the fusion junction.

In some embodiments, the method further comprises detecting the level of the polynucleotide.

In some embodiments, the nucleic acid sample is derived from a subject having gastric cancer.

The present invention also provides a primer set for detecting a fusion gene of HNF4G and RSPO2, comprising: a first primer directed to a first sequence for HNF4G, and a second primer directed to a second sequence for RSPO2; or a junction primer directed to a fragment containing the fusion junction of HNF4G and RSPO2, and a non junction primer directed to the first sequence for HNF4G or the second sequence for RSPO2.

In some embodiments, the first primer or the second primer is directed to a region at least 80 bp upstream or downstream of the fusion junction of the fusion gene, wherein the fusion junction comprises CCACAGCCTT|gt-tcgtggcg (SEQ ID NO: 3).

In some embodiments, the first primer and the second primer are useful of amplifying an amplicon having a length of about 200 bp to 400 bp. In some embodiments, the first primer is directed to SEQ ID NO: 1 or SEQ ID NO: 6; the second primer is directed to SEQ ID NO: 2.

The present invention also provides a probe set for detecting a fusion gene of HNF4G and RSPO2, comprising: a first probe directed to a first sequence for HNF4G, and a second probe directed to a second sequence for RSPO2; or a junction probe directed to a fragment containing the fusion junction of HNF4G and RSPO2.

The present invention further provides a kit for detecting a fusion gene of HNF4G and RSPO2, comprising the aforementioned primer set or probe set.

The present invention further provides an animal model for a human disease positive for a fusion gene of HNF4G and RSPO2, comprising a human xenograft comprising the fusion gene.

The present invention further provides a method of assessing effect of a test agent on a human disease positive for a fusion gene of HNF4G and RSPO2, comprising: obtaining the aforementioned animal model for the human disease; administering the test agent to the animal model; determining the effect of the test agent on the human xenograft; and assessing effect of the test agent on the human disease. In some embodiments, the test agent is a wnt pathway antagonist. In some embodiments, the therapeutic agent is a wnt pathway antagonist. In some embodiments, the test agent targets RSPO2 or the fusion gene of HNF4G and RSPO2. In certain embodiments, the therapeutic agent is a small interference RNA (siRNA) that binds RSPO2 or the fusion gene of HNF4G and RSPO2. In some embodiments, the test agent is a monoclonal antibody or an antigen binding fragment thereof that binds RSPO2 or the fusion gene of HNF4G and RSPO2. In some embodiments, the disease is cancer.

The present invention further provides a method of assessing effect of a test agent on fusion gene of HNF4G and RSPO2, comprising: obtaining a cell positive for the fusion gene; exposing the cell to the test agent; and determining the effect of the test agent on the fusion gene or on the cell. In some embodiments, the test agent is a wnt pathway antagonist. In some embodiments, the therapeutic agent is a wnt pathway antagonist. In some embodiments, the test agent targets RSPO2 or the fusion gene of HNF4G and RSPO2. In certain embodiments, the test agent is a small interference RNA (siRNA) that binds RSPO2 or the fusion gene of HNF4G and RSPO2. In some embodiments, the test agent is a monoclonal antibody or an antigen binding fragment thereof that binds RSPO2 or the fusion gene of HNF4G and RSPO2. In some embodiments, the disease is cancer.

The present invention also provides a method of identifying an agent useful for treating a disease associated with a fusion gene of HNF4G and RSPO2, comprising: providing a cell positive for the fusion gene, exposing the cell to candidate agents, and identifying an agent that modulates the biological activity of the fusion gene or the gene product thereof. In some embodiments, the agent is a wnt pathway antagonist. In some embodiments, the agent is a wnt pathway antagonist. In some embodiments, the agent targets RSPO2 or the fusion gene of HNF4G and RSPO2. In certain embodiments, the agent is a small interference RNA (siRNA) that binds RSPO2 or the fusion gene of HNF4G and RSPO2. In some embodiments, the agent is a monoclonal antibody or an antigen binding fragment thereof that binds RSPO2 or the fusion gene of HNF4G and RSPO2. In some embodiments, the disease is cancer.

The present invention also provides a method of treating a disease associated with a fusion gene of HNF4G and RSPO2, comprising administering an effective amount of a therapeutic agent capable of modulating the biological activity of the fusion gene or the gene product thereof, thereby treating the disease. In some embodiments, the therapeutic agent is a wnt pathway antagonist. In some embodiments, the therapeutic agent targets RSPO2 or the fusion gene of HNF4G and RSPO2. In certain embodiments, the therapeutic agent is a small interference RNA (siRNA) that binds RSPO2 or the fusion gene of HNF4G and RSPO2. In some embodiments, the therapeutic agent is a monoclonal antibody or an antigen binding fragment thereof that binds RSPO2 or the fusion gene of HNF4G and RSPO2. In some embodiments, the disease is cancer.

BRIEF DESCRIPTION OF FIGURES

FIG. 2 is the junction sequence (SEQ ID NO: 4) of the HNF4G-RSPO2 gene fusion in GA3055. Sequence in capital letters is from HNF4G, sequence in small letters is from RSPO2. The fusion junction site is indicated by "|".

FIG. 3 shows activation of RSPO2 gene expression by HNF4G-RSPO2 gene fusion in GA3055.

FIG. 4 shows the HNF4G-RSPO2 gene fusion junction sequence (SEQ ID NO:5) and location of the primers used to validate fusion by PCR. Capital letters represent sequence of HNF4G; Small letters represent sequence of RSPO2; Boxed sequences represent sequences of PCR primers.

DETAILED DESCRIPTION OF THE INVENTION

Figure 1:
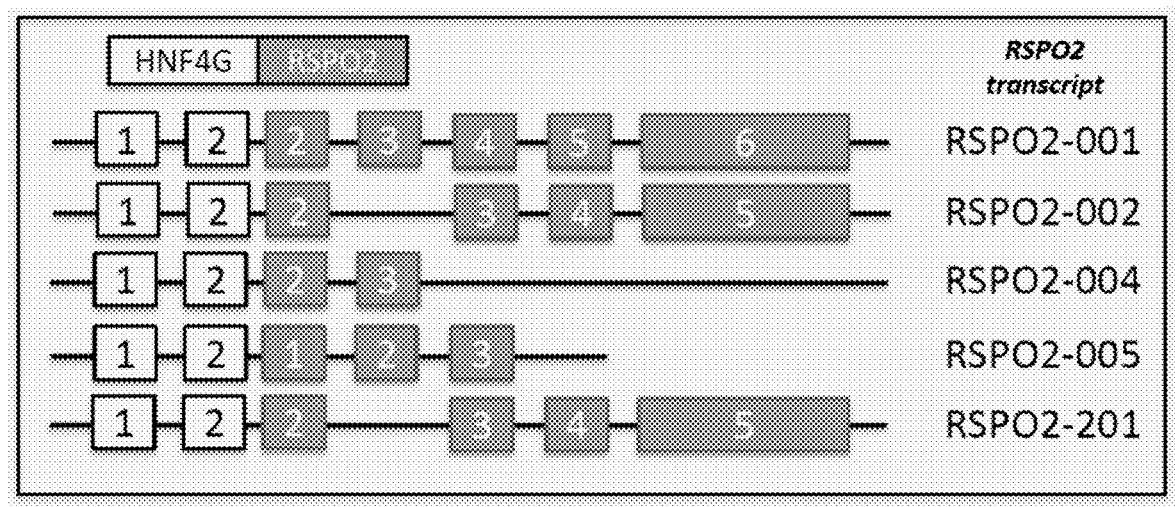
FIG. 1 is a schematic representation of the HNF4G-RSPO2 gene fusion in GA3055. Exon 2 of the HNF4G gene was fused to Exon 2 (or Exon 1 in the case of the RSPO2-005 transcript) of the RSPO2 gene.

The present disclosure is at least partially based on the discovery of HNF4G gene as a novel fusion partner of RSPO2 gene. In particular, the novel fusion gene of HNF4G and RSPO2 is found in gastric tumor.

The present disclosure provides methods of detecting the fusion gene of HNF4G and RSPO2, primer sets and probe sets useful for detecting such fusion gene or its gene product. In vitro and in vivo testing methods are also provided to assess or identify active agents for inhibiting or reducing the fusion gene or its gene product.

Fusion Gene

The present disclosure provides novel fusion genes of HNF4G and RSPO2. "Fusion gene" and "gene fusion" are used interchangeably herein and are intended to encompass both DNA and RNA, including but not limited to fusion of two or more separate genes at DNA level (such as genomic DNA or cDNA), RNA level (such as mRNA). In certain embodiments, the two genes are fused at genomic DNA level due to chromosome rearrangement, such as a translocation, interstitial deletion, or chromosomal inversion. Fusion gene may be transcribed and/or translated to its gene product, which can be RNA or protein.

The fusion genes provided herein comprise a first sequence for HNF4G covalently linked to a second sequence for RSPO2. "HNF4G" as used herein can refer to the gene (e.g. the DNA sequence) or the gene transcript (e.g. mRNA). "RSPO2" as used herein can refer to the gene (e.g. the DNA sequence), the gene transcript (e.g. mRNA), or the protein product (i.e, the amino acid sequence), and people skilled in the art can understand the meaning from the context. "Encoding sequence" as used herein refers to the polynucleotide sequence which encodes at least a fragment of a protein product. "Noncoding sequence" as used herein refers to the polynucleotide sequence which does not encode protein, or the polynucleotide sequence which is transcribed into functional noncoding RNA. The sequence can be a DNA sequence such as genomic DNA or cDNA, and can also be a RNA sequence such as mRNA. The fusion of the two encoding sequences can be in frame, such that after being translated into its protein product, a protein fragment of HNF4G is fused to a protein fragment of RSPO2. In the fusion gene, the sequence for HNF4G can be 5' upstream or 3' downstream of the encoding sequence for RSPO2. In certain embodiments, the first sequence for HNF4G is 5' upstream of the second sequence for RSPO2. In certain embodiments, the first sequence is a noncoding sequence, and the second sequence is an encoding sequence.

The sequence comprises one or more exons. Sequences of the exons of HNF4G and RSPO2 can be obtained from publicly available databases such as Ensembl. In brief, Ensembl database provides transcripts for a given gene such as HNF4G or RSPO2, and for each transcript, each of the exon sequences is sequentially numbered starting from 5' to 3' direction, and the exon sequence is provided in which its start and end on the chromosome location are also identified. In some cases, an exon sequence may have a different exon numbering in a different transcript. For example, an exon sequence may be numbered as exon 1 in transcript 1 but numbered as exon 2 in transcript 2, although the exon sequence may still be substantially the same.

In some embodiments, the first sequence for HNF4G comprises (a) at least a portion of exon 2 of a HNF4G gene transcript as shown in ENST00000396419, or (b) at least a portion of exon 3 of a HNF4G gene transcript as shown in ENST00000494318. As used herein, a gene transcript is identified by its Ensembl number, and the corresponding sequence of which is available on the world wide web at the Ensemble organization website (http://asia.ensembl.org/). For more details about Ensemble database, please see Flicek et al, Nucleic Acids Research 2014, 42 Database issue: D749-D755, which is incorporated herein by reference to its entirety.

In certain embodiments, the first sequence for HNF4G comprises a sequence comprising at least a portion of exon 2 of a HNF4G gene transcript as shown in ENST00000396419, and the sequence comprises SEQ ID NO: 1 (5'-3'):

AGCTCCGGGAGCGGCCCGCGCAGGAGCACCAGCGAAAGCAGCCAGTC

TGAGATATTGACACTACAGAAAAAACTGACAGCTTACTCCTTGTATT

GATTCTACTCTTCTCTACAAATATAGACTCCGTTCCCTACCACAGCC

TT.

In certain embodiments, the first sequence for HNF4G comprises a sequence comprising at least a portion of exon 3 of a HNF4G gene transcript as shown in ENST00000494318, and the sequence comprises SEQ ID NO: 6 (5'-3'):

GCGGCCCGCGCAGTGATTGCTGCCTTGACCGTCCCTGCTCTTGAAGA

GCACCAGCGAAAGCAGCCAGTCTGAGATATTGACACTACAGAAAAAA

CTGACAGCTTACTCCTTGTATTGATTCTACTCTTCTCTACAAATATA

GACTCCGTTCCCTACCACAGCCTT.

In some embodiments, the second sequence for RSPO2 comprises: (a) at least a portion of exon 2 of a RSPO2 gene transcript as shown in ENST00000276659, ENST00000517781, ENST00000522333, or ENST00000378439, or (b) at least a portion of exon 1 of a RSPO2 gene transcript as shown in ENST00000521956. In certain embodiments, the second sequence for RSPO2 gene comprises or consists of: i) exon 2, exon 3, exon 4, exon 5, and exon 6 of a RSPO2 gene transcript as shown in ENST00000276659; ii) exon 2, exon 3, exon 4, and exon 5 of a RSPO2 gene transcript as shown in ENST00000517781; iii) exon 2 and exon 3 of a RSPO2 gene transcript as shown in ENST00000522333; iv) exon 1, exon 2, and exon 3 of a RSPO2 gene transcript as shown in ENST00000521956; or v) exon 2, exon 3, exon 4, and exon 5 of a RSPO2 gene transcript as shown in ENST00000378439.

In certain embodiments, the second sequence for RSPO2 comprises SEQ ID NO: 2 (5'-3'):

GTTCGTGGCGGAGAGATGCTGATCGCGCTGAACTGACCGGTGCGGCC

CGGGGGTGAGTGGCGAGTCTCCCTCTGAGTCCTCCCCAGCAGCGCGG

CCGGCGCCGGCTCTTTGGGCGAACCCTCCAGTTCCTAGACTTTGAGA

GGCGTCTCTCCCCCGCCCGACCGCC.

In certain embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000276659, and the exon 2 of the HNF4G gene transcript ENST00000396419 or the exon 3 of the HNF4G gene transcript ENST00000494318 fuses to the exon 2 of the RSPO2 gene transcript.

In certain embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000517781, and the exon 2 of the HNF4G gene transcript ENST00000396419 or the exon 3 of the HNF4G gene transcript ENST00000494318 fuses to the exon 2 of the RSPO2 gene transcript;

In certain embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000522333, and the exon 2 of the HNF4G gene transcript ENST00000396419 or the exon 3 of the HNF4G gene transcript ENST00000494318 fuses to the exon 2 of the RSPO2 gene transcript.

In certain embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 2 of the RSPO2 gene transcript as shown in ENST00000378439, and the exon 2 of the HNF4G gene transcript ENST00000396419 or the exon 3 of the HNF4G gene transcript ENST00000494318 fuses to the exon 2 of the RSPO2 gene transcript.

In certain embodiments, the first sequence for HNF4G comprises a sequence selected from a) at least a portion of exon 2 of the HNF4G gene transcript as shown in ENST00000396419, and b) at least a portion of exon3 of the HNF4G gene transcript as shown in ENST00000494318, and the second sequence for RSPO2 comprises at least a portion of exon 1 of the RSPO2 gene transcript as shown in ENST00000521956, and the exon 2 of the HNF4G gene transcript ENST00000396419 or the exon 3 of the HNF4G gene transcript ENST00000494318 fuses to the exon 1 of the RSPO2 gene transcript.

The site where the HNF4G sequence fuses to the RSPO2 sequence is referred to as fusion junction. In some embodiments, the fusion genes provided herein comprise a fusion junction of CCACAGCCTT|gttcgtggcg (SEQ ID NO: 3), in which the HNF4G sequence is in capital letters and the RSPO2 sequence is in lower case letters. In some embodiments, the fusion genes comprise SEQ ID NO: 4, in which the HNF4G sequence is in capital letters and the RSPO2 sequence is in lower case letters (see FIG. 2). In certain embodiments, the fusion genes comprise SEQ ID NO: 5, in which the HNF4G sequence is in capital letters and the RSPO2 sequence is in lower case letters (see FIG. 4).

Certain specific examples of the fusion genes are illustrated in the below Table 1 and also in FIG. 1. The exons which are fused together in the fusion genes are marked in bold font. All the 5 fusion genes share an identical fusion junction which is SEQ ID NO: 3. FIG. 1 shows an exemplary arrangement and fusion of the exons in the fusion genes.

TABLE 1

| Fusion genes | HNF4G exons | RSPO2 exons |
|---|---|---|
| HNF4G-004-RSPO2-001 | Exons 1 and 2 in ENST00000396419 | Exons 2-6 in ENST00000276659 |
| HNF4G-004-RSPO2-002 | Exons 1 and 2 in ENST00000396419 | Exons 2-5 in ENST00000517781 |
| HNF4G-004-RSPO2-004 | Exons 1 and 2 in ENST00000396419 | Exons 2 and 3 in ENST00000522333 |
| HNF4G-004-RSPO2-005 | Exons 1 and 2 in ENST00000396419 | Exons 1-3 in ENST00000521956 |
| HNF4G-004-RSPO2-201 | Exons 1 and 2 in ENST00000396419 | Exons 2-5 in ENST00000378439 |

Methods of Detecting the Fusion Gene and/or the Gene Product Thereof

Provided herein are also methods of detecting a fusion gene of HNF4G and RSPO2 provided herein in a nucleic acid-containing sample, comprising: contacting the sample with a detecting agent which specifically detects a target polynucleotide comprising a fusion of a first sequence for HNF4G and a second sequence for RSPO2, and detecting the presence of the target polynucleotide.

The nucleic acid-containing sample can be derived from a cell or a tissue from a subject. "Nucleic acid" as used herein can be a polymer of RNA or a polymer of DNA. The sample may contain isolated nucleic acid such as isolated RNA or cDNA. Alternatively, the sample may contain nucleic acid in its natural or unpurified or unamplified state, for example, the sample may be an isolated cell or tissue, optionally pretreated to release the nucleic acid contained therein. In a further embodiment, the nucleic acid in the sample may be amplified, e.g. by PCR reaction or reverse transcription.

In certain embodiments, the sample is derived from a subject suspect of having gastric tumor or cancer. The sample can be any suitable biological material collected from the subject, such as body fluid (e.g. blood) and a biopsy sample (e.g. cells or tissues from a disease affected area). In certain embodiments, the sample is derived from a gastric tumor or cancer cell or tissue. The sample can be treated to extract the nucleic acid.

In the detecting method, the sample is contacted with an oligonucleotide which specifically detects a target polynucleotide comprising the fusion gene. The target polynucleotide can be cDNA or mRNA, depending on the type of nucleic acid contained in the sample. The target polynucleotide can comprises any of the fusion genes as provided herein. In certain embodiments, the target polynucleotide comprises any of SEQ ID NOs: 3-9 or the RNA version thereof.

The target polynucleotide can be detected based on any suitable methods known in the art, for example but not limited to, hybridization-based methods and amplification-based methods. Hybridization-based methods usually involve using a probe to hybridize and detect the target sequence. Examples of hybridization-based methods include, Northern blot, DNA microarray, whole genome sequencing, RNA sequencing (RNA-seq), quantitative real time PCR (qRT-PCR), digital multiplexed gene expression analysis method (see, e.g., Kulkarni M M, Curr Protoc Mol Biol. 2011 April, Chapter 25:Unit25B.10.), FISH method (Fluorescence In Situ Hybridization), CISH (Chromogenic In Situ Hybridization) method, SISH (silver in situ hybridization) methods, and the like. Amplification-based methods usually involve using primers, polymerase and mixture of nucleotide monomers to synthesize nascent polynucleotide chain based on the base sequence of the target template polynucleotide. Examples of amplification-based methods include, PCR (polymerase chain reaction), LCR (Ligase chain reaction), SDA (Strand displacement amplication), isothermal and chimeric primer-initiated amplification of nucleic acids), loop-mediated isothermal amplification, transcription-mediated amplification and the like.

In certain embodiments, the detecting step involves an amplification step. In such case, the detecting agent comprises at least a pair of primers which can hybridize to the target polynucleotide and amplify a target region encompassing the fusion junction in the presence of a polymerase. In one embodiment, the detecting agent comprises a first primer directed to the first sequence for HNF4G, and a second primer directed to the second sequence for RSPO2. As used herein, a primer or a probe "directed to" a sequence, means that the primer or the probe has sufficient identity with or complementarity to at least a portion of the sequence such that the primer or the probe can specifically hybridize to the sequence or to its complementary strand. "Specifically hybridize" as used herein means the primer or probe can hybridize to the intended sequence under stringent conditions. "Stringent condition" as used herein refers to hybridizing at 42° C. in a solution consisting of 5×SSPE, 5×Denhardt's solution, 0.5% SDS, and 100 ug/mL denatured salmon sperm DNA, and then washing at 42° C. with a solution comprising 0.5×SSC and 0.1% SDS.

In another embodiment, the detecting agent comprises a junction primer directed to a fragment containing the fusion junction, and a non-junction primer directed to the first or the second sequence. The junction primer would specifically hybridize to the fusion junction, thereby specifically enabling the amplification when the target polynucleotide is present. Otherwise, if the nucleic acid in the sample does not contain the target polynucleotide, the junction primer would not specifically hybridize to its target sequence, and cannot effectuate a meaningful amplification.

After amplification by a suitable nucleic acid amplification method such as PCR, the amplification product is detected. In certain embodiments, the amplification product has a length of 100 bp-1500 bp (e.g. 100 bp-1000 bp, 100 bp-900 bp, 100 bp-800 bp, 100 bp-700 bp, 100 bp-600 bp, 100 bp-500 bp, 100 bp-400 bp, 100 bp-350 bp, 100 bp-300 bp, 200 bp-1000 bp, 200 bp-900 bp, 200 bp-800 bp, 200 bp-700 bp, 200 bp-600 bp, 200 bp-500 bp, 200 bp-400 bp, 200 bp-350 bp, 200 bp-300 bp, etc.). In certain embodiments, the presence of the amplification product would be indicative of the presence of the target polynucleotide. In certain embodiments, the molecular weight or size or sequence of the amplification product is further detected, and a desired size or sequence of the amplification product indicates presence of the target polynucleotide.

When the target polynucleotide is RNA, the amplification step may optionally further comprises a reverse transcription step to produce cDNA of the RNA in the sample. The cDNA is then amplified using the primers to allow detection of presence of the fusion junction.

The primers provided herein have a length of about 10-100 bp (e.g. 10-50 bp, 10-40 bp, 10-30 bp, 10-25 bp, and etc.). In certain embodiments, the first primer comprises at least 10 (e.g. 10, 11, 12, 13, 14, 15, 16, 17, 18, 19, 20 etc.) consecutive nucleotides complementary to an equal length portion of SEQ ID NO: 1 or SEQ ID NO: 6, and the second primer comprises at least 10 (e.g. 10, 11, 12, 13, 14, 15, 16, 17, 18, 19, 20 etc.) consecutive nucleotides of an equal length portion of SEQ ID NO: 2. In certain embodiments, the first primer comprises at least 10 (e.g. 10, 11, 12, 13, 14, 15, 16, 17, 18, 19, 20 etc.) consecutive nucleotides of an equal length portion of SEQ ID NO: 1 or SEQ ID NO: 6, and the second primer comprises at least 10 consecutive nucleotides (e.g. 10, 11, 12, 13, 14, 15, 16, 17, 18, 19, 20 etc.) complementary to an equal length portion of SEQ ID NO: 2.

In certain embodiments, the first primer or the second primer is directed to a region at least 80 bp upstream or downstream of the fusion junction of the fusion gene. In certain embodiments, the fusion gene comprises a fusion junction of SEQ ID NO: 3. In certain embodiments, the first primer and the second primer are useful of amplifying an amplicon having a length of about 200 bp to 400 bp. In certain embodiments, the first primer is directed to SEQ ID NO: 1 or SEQ ID NO: 6 and the second primer is directed to SEQ ID NO: 2. In certain embodiments, the first primer and the second primer is selected from the group consisting of 5' CAGGAGCACCAGCGAAAG 3' (SEQ ID NO: 7), and 5' TGAGGGCAAAGGAGAAAAGG 3' (SEQ ID NO: 8).

The junction primer comprises at least 6 (e.g. 6, 7, 8, 9, or 10) consecutive nucleotides of SEQ ID NO: 3, or comprises at least 6 consecutive nucleotides complementary to an equal length portion of SEQ ID NO: 3. In certain embodiments, the junction primer comprises SEQ ID NO: 3 or is complementary to SEQ ID NO: 3. The non junction primer can be designed based on the desired length of the amplification product, once the junction primer is determined. For example, when it is desired to have a 300 bp amplification product, then the non-junction primer can be designed to be complementary to the target polynucleotide about 300 bp 5' upstream the fusion junction or 3' downstream of the fusion junction.

In certain embodiments, the detecting step involves a hybridization step. Probes can be designed to specifically hybridize to the target polynucleotide, thereby allowing its detection. Probes provided herein can have a suitable length, for example, about 20-200 bp (e.g. 20-190 bp, 20-150 bp, 20-120 bp, 20-100 bp, 20-90 bp, 20-80 bp, 20-70 bp, 20-60 bp, 20-50 bp, 20-40 bp, and etc.).

In certain embodiments, the detecting agent comprises a first probe directed to the first sequence for HNF4G, and a second probe directed to the second sequence for RSPO2. In certain embodiments, the first probe comprises at least 10 (e.g. 10, 11, 12, 13, 14, 15, 16, 17, 18, 19, 20 etc.) consecutive nucleotides directed to an equal length portion of SEQ ID NO: 1 or SEQ ID NO: 6, and the second probe comprises at least 10 (e.g. 10, 11, 12, 13, 14, 15, 16, 17, 18, 19, 20 etc.) consecutive nucleotides directed to an equal length portion of SEQ ID NO: 2. In an illustrative example, one of the first and the second probes can be a capture probe which further comprises an immobilizing moiety capable of associating with a substrate through a covalent or a non-covalent bond, and the other probe can be a detecting probe which further comprises a detectable label. The capture probe can be first contacted with the sample to allow hybridization with the nucleic acid, then the complex is immobilized on a substrate via the immobilizing moiety on the capture probe, and the unbound molecules are removed. The detecting probe is then added to the immobilized complexes to allow hybridization to occur. After washing away the excess probe, the detectable label immobilized on the substrate is detected. Illustrative examples of the immobilizing moiety include, but are not limited to, biotin, streptavidin, antigen, antibody, protein A, protein G, oligonucleotide, etc. The detectable label on the detecting probe can be, for example, fluorescent dye, radioisotope, antibody, enzyme, and oligonucleotide (e.g. an oligonucleotide barcode). In another illustrative example, one of the first and the second probes further comprises a fluorescent dye and the other probe comprises a quencher. After both probes are bound to the target polynucleotide, the two probes are in proximity to each other such that the quencher on one probe quenches the fluorescent signal of the dye on the other probe. Illustrative examples of fluorescent dye include, but are not limited to fluorescein isothiocyanate (FITC), Alexa 488, Alexa 532, cy3, cy5, 6-joe, EDANS; rhodamine 6G (P6G) and its derivatives (tetramethyirhodamine (TMR), tetramethylrhodamine isothiocyanate (TMRITC), x-rhodamine, Texas red, "BODIPY FL" (trade name, product of Molecular Probes, Inc. (Eugene, Oreg., U.S.A.), "BODIPY FL/C3" (trade name, product of Molecular Probes, Inc.), "BODIPY EL/C6" (trade name, product of Molecular Probes, Inc.), "BODIPY 5-FAM" (trade name, product of Molecular Probes, Inc.), "BODIPY TMR" (trade name, product of Molecular Probes, Inc.), and derivatives thereof (for example, "BODIPY TR" (trade name, product of Molecular Probes, Inc.), "BODIPY R6G" (trade name, product of Molecular Probes, Inc.), "BODIPY 564" (trade name, product of Molecular Probes, Inc.), and "BODIPY 581" (trade name, product of MolecularProbes, Inc.)). Illustrative examples of the quencher include, but are not limited to, Dabcyl, "QSY7" (Molecular Probes), "QSY33" (Molecular Probes), Ferrocene and its derivatives, methyl viologen, and N,N'-dimethyl-2,9-diazopyrenium and the like.

In certain embodiments, the detecting agent comprises a junction probe directed to a fragment containing the fusion junction. The junction probe comprises at least 6 (e.g. 6, 7, 8, 9, or 10) consecutive nucleotides of an equal length of SEQ ID NO: 3, or comprises at least 6 consecutive nucleotides complementary to an equal length of SEQ ID NO: 3. The junction probe may further comprise a detectable label. In an illustrative example, the nucleic acid in the sample may be immobilized on a substrate, and then contacted with the probe which recognizes the fusion junction. After washing away the unreacted probes, the substrate can be detected for presence of the probe, which can indicate the presence of the fusion junction of the fusion gene. In another illustrative example, the junction probe can comprise both a fluorescent dye and a quencher, such that the quencher quenches the fluorescence of the dye when the probe is intact. The probe can be used in an amplification method in which a target region encompassing the fusion junction is to be amplified using a polymerase having 5'-3' exonuclease activity (such as Taq polymerase). During the amplification, the probe which hybridizes to the fusion junction can be degraded by the polymerase as it proceeds along the target polynucleotide, thereby separating the fluorescent dye and the quencher on the probe, and allow the fluorescent dye to emit its signal to be detected.

In another aspect, the present disclosure further provides methods of detecting the fusion gene provided herein in a protein-containing sample, comprising contacting the sample with a detecting agent which specifically detects a fusion protein encoded by the fusion gene, and detecting the presence of the fusion protein.

The presence and level of the fusion protein encoded by the fusion gene can be detected. For example, the sample may be contacted with an antibody specific for the fusion protein, and formation of a complex between the antibody and the fusion protein can be detected using methods known in the art, such as, for example, an immunohistochemistry assay, western blot method, ELISA, ELIFA, fluorescence immunoassay method, radioimmunoassay method, enzymatic immunoassay method, double antibodies sandwich method, and etc.

Kits

The primer sets or probe sets or junction probe as provided herein are useful in detecting the fusion gene of HNF4G and RSPO2. Therefore, another aspect of the present disclosure relates to kits comprising the primer sets, or the probe sets, or the junction probe described herein.

In certain embodiments, the kits comprise a first primer directed to a first sequence for HNF4G, and a second primer directed to a second sequence for RSPO2. In certain embodiments, the kits comprise a junction primer directed to a fragment containing the fusion junction of HNF4G and RSPO2, and a non-junction primer directed to the first sequence for HNF4G or the second sequence for RSPO2.

In certain embodiments, the kits comprise a first probe directed to a first sequence for HNF4G, and a second probe directed to a second sequence for RSPO2. In certain embodiments, the kits comprise a junction probe directed to a fragment containing the fusion junction.

The kits provided herein may further comprise one or more components useful for the detection, for example, polymerase, a buffer useful for amplification, and/or a buffer useful for probe hybridization.

Methods of Use

The present disclosure further provides methods of using the fusion gene.

The gene fusion of HNF4G-RSPO2 is an intrachromosome rearrangement on human Chr.8. The present inventors have found that this fusion gene of HNF4G and RSPO2 is present in a gastric cancer tissue, while previous R-Spondin gene fusions were described only in colorectal tumor samples. Thus, the fusion gene of HNF4G and RSPO2 may be a druggable target for a disease positive for the fusion gene, and in particular, for a disease associated with wnt signaling.

In one aspect, the present disclosure provides methods of identifying a candidate agent useful for treating a disease positive for a fusion gene of HNF4G and RSPO2 in a subject, comprising: providing a cell positive for the fusion gene, exposing the cell to candidate agents, and identifying a candidate agent that modulates the biological activity of the fusion gene or the gene product thereof.

The term "modulate" used herein refers to up-regulation or down-regulation of expression level and/or biological activity of the fusion gene or its gene product. In certain embodiments, the cell is derived from a tissue or a sample of a subject positive for a fusion gene of HNF4G and RSPO2. In certain embodiments, the cell is derived from a tissue or sample of a subject with gastric tumor or gastric cancer who is detected positive for the fusion gene. In certain embodiments, the cell can be genetically engineered to comprise the fusion gene. In certain embodiments, the candidate agents may include, but not limited to, nucleic acids, small organic or inorganic molecules, and antibodies or the antigen binding fragment thereof. In certain embodiments, the candidate agent is a wnt pathway antagonist. In certain embodiments, the candidate agent targets RSPO2 or the fusion gene of HNF4G and RSPO2. In certain embodiments, the candidate agent is a small interference RNA (siRNA) that binds RSPO2 or the fusion gene of HNF4G and RSPO2. In certain embodiments, the candidate agent is a monoclonal antibody or an antigen binding fragment thereof that binds RSPO2 or the fusion gene of HNF4G and RSPO2.

In certain embodiments, the present disclosure further provides methods of assessing effect of a test agent on fusion gene of HNF4G and RSPO2, comprising: obtaining a cell positive for the fusion gene; exposing the cell to the test agent; and determining the effect of the test agent on the fusion gene or on the cell. Effect of the test agent on the fusion gene can be, for example, reduce or elevate the expression level and/or the biological activity of the fusion gene or its gene product.

In another aspect, the present disclosure provides methods of treating a disease associated with a fusion gene of HNF4G and RSPO2, comprising administering an effective amount of a therapeutic agent capable of modulating the biological activity of the fusion gene or the gene product thereof, thereby treating the disease.

In certain embodiments, the disease is a proliferative disease which involves uncontrolled cell growth. In certain embodiments, the disease is tumor or cancer. In certain embodiments, the disease is gastric tumor or gastric cancer.

As used herein, the term "treating" or "treatment" refers to one or more therapeutic activities that are conducted in order to have one or more desired or beneficial results and can be performed either for prophylaxis or during the course of clinical pathology. In this invention, desired or beneficial treatment include, but are not limited to, one or more of the following: preventing onset or recurrence of disease, alleviation of one or more symptoms resulting from the disease, diminishment of pathological consequences of the disease, preventing metastasis, amelioration of the disease, increase of the quality of life of those suffering from the disease, decrease of the dose of other medications required to treat the disease, delaying the disease progression, and/or prolongation of the survival of those suffering from the disease. In certain embodiments, the therapeutic agent can be any one of an antibody or an antigen binding fragment thereof, a binding protein, a small organic or inorganic molecule, a nucleic acid and any combination thereof.

In certain embodiments, the therapeutic agent includes, but not limited to, a nucleic acids, a small organic or inorganic molecule, and an antibodies or an antigen binding fragment thereof. In certain embodiments, the therapeutic agent is a wnt pathway antagonist. In certain embodiments, the therapeutic agent targets RSPO2 or the fusion gene of HNF4G and RSPO2. In certain embodiments, the therapeutic agent is a small interference RNA (siRNA) that binds RSPO2 or the fusion gene of HNF4G and RSPO2. In some embodiments, the therapeutic agent is a monoclonal antibody or an antigen binding fragment thereof that binds RSPO2 or the fusion gene of HNF4G and RSPO2. The present invention further provides a method of assessing effect of a test agent on fusion gene of HNF4G and RSPO2, comprising: obtaining a cell positive for the fusion gene; exposing the cell to the test agent; and determining the effect of the test agent on the fusion gene or on the cell.

As used herein, the expression "effect of test agent" can include the effect on the expression level or biological activity of the fusion gene, and/or on the expression level or biological activity of the protein product of the fusion gene.

In some embodiments, the test agent is a wnt pathway antagonist. In some embodiments, the therapeutic agent is a wnt pathway antagonist. In some embodiments, the test agent targets RSPO2 or the fusion gene of HNF4G and RSPO2, or the gene product of the fusion gene. In certain embodiments, the test agent is a small interference RNA (siRNA) that binds RSPO2 or the fusion gene of HNF4G and RSPO2. In some embodiments, the test agent is a monoclonal antibody or an antigen binding fragment thereof that binds RSPO2 or the fusion gene of HNF4G and RSPO2. In certain embodiments, the disease is tumor or cancer. In certain embodiments, the disease is gastric tumor or gastric cancer.

Animal Model and Use of the Animal Model

In another aspect, the present disclosure provides animal models for a human disease positive for a fusion gene of HNF4G and RSPO2, comprising a human xenograft comprising the fusion gene provided herein.

The human xenograft comprises a cell or tissue positive for a fusion gene of HNF4G and RSPO2, which, after being grafted to the animal, can simulate or mimic the human disease or a lesion of the disease associated with the fusion gene. The xenograft can be grafted to the animal model using any suitable methods known in the art, for example, by grafting cells subcutaneously, intraperitoneally, or intravenously through injection; or alternatively, by implanting a fraction of tissue through surgery. In some embodiments, the xenografts are cancerous cells, and are grafted to the animal model through subcutaneously injection. In certain embodiments, the xenografted are cells or tissues from the human gastric tumor or gastric cancer. Presence of the fusion gene can lead to difference in the disease, for example, different severity of the disease, different subtypes of the disease, different stage of the disease, different responsiveness to a particular therapeutic agent, and so on. As such, the animal models provided herein are particularly useful in studying a human disease associated with the fusion gene, and also in evaluating responsiveness of the disease to a particular therapeutic agent. In certain embodiments, the disease is tumor or cancer. In certain embodiments, the disease is gastric tumor or gastric cancer.

The term "animal" as used herein refers to all vertebrate animals except human, preferably a mammal, such as a dog, a pig, a rabbit, or a rodent (e.g. a mouse, a rat, a hamster, a guinea pig or such like). In certain embodiments, the animal model is a mammal. In certain embodiments, the animal model is a rodent. In certain embodiments, the rodent is a mouse, a rat, a guinea pig or a hamster. In certain embodiments, the animal model is immuno-deficient. The immuno-deficient animal is depleted of active endogenous T cells, active endogenous B cells and active endogenous Natural Killer cells. Examples of immuno-deficient animals include, for example: T lymphocytes deficient animals (eg. BALB/c nude mice, C57BL nude mice, NIH nude mice, nude rat, etc.); B lymphocytes deficient animals (eg. CBA/N mice); NK cell deficient animal (eg. Beige mice); combined immuno-deficient animal (e.g. severe combined immuno-deficient (SCID) mice (combined T and B lymphocytes deficient), Beige/Nude (combined T lymphocytes and NK cells deficient), SCID Beige/SCID NOD mice (combined T, B lymphocytes and NK cells deficient)), and animals which are treated or manipulated to have an immune system which resembles that in any the above-mentioned immuno-deficient animals.

In another aspect, the present disclosure provides methods of assessing effect of a test agent on a human disease positive for a fusion gene of HNF4G and RSPO2, comprising: obtaining the animal model for the human disease provided herein; administering the test agent to the animal model; determining the effect of the test agent on the human xenograft; and assessing effect of the test agent on the human disease.

In certain embodiments, the test agent may include, but not limited to, nucleic acids, small organic or inorganic molecules, and antibodies or the antigen binding fragment thereof. In some embodiments, the test agent is a wnt pathway antagonist. In some embodiments, the therapeutic agent targets RSPO2 or the fusion gene of HNF4G and RSPO2. In certain embodiments, the test agent is a small interference RNA (siRNA) that binds RSPO2 or the fusion gene of HNF4G and RSPO2. In some embodiments, the test agent is a monoclonal antibody or an antigen binding fragment thereof that binds RSPO2 or the fusion gene of HNF4G and RSPO2. In certain embodiments, the disease is tumor or cancer. In certain embodiments, the disease is gastric tumor or gastric cancer. The test agent can be administered to the animal model at one or more suitable doses, and the effects on the animal model can be assessed.

The test agent can be administered to the animal model in any suitable manner known in the art. In certain embodiments, the test agent can be administered orally, gastrointestinally, topically, intrarectally, intravenously, transdermally, transmucosally, etc. In certain embodiments, the term "suitable dose" or "dose" refers to physically discrete units that contain a predetermined quantity of test agent, which is calculated to produce a desired effect. In certain embodiments, the animal is administered with a single dose or multiple doses. In certain embodiments, the assessment is conducted by a single or multiple times. In certain embodiments, the assessment is carried out in samples or specimens (e.g., blood, a biopsy) from the animals before and after administration of the test agents. In some embodiments, the test is carried out by observing the physical changes (eg. weight loss/gain, mental state) of the animal before and after administration of the test agents. In certain embodiments, the assessment is conducted by comparing the size/weight of the xenograft and/or comparing presence and/or level of certain biomarker in the animal model before and after administration of the test agents.

The following examples are presented to illustrate the present invention. They are not intended to limiting in any manner.

EXAMPLES

Example 1: Genomic Profiling of Patient Derived Xenograft (PDX) Models

Patient derived xenografts (PDXs) mirrors patients' pathology and genetic profiles, thus valued as predictive experimental models for studying oncogenesis and personalized treatments. To better understand underlying mechanisms of cancer development, and to identify biomarkers and molecular targets for effective cancer diagnosis and treatment, genomic profiling is performed on a collection of 50 PDX gastric cancer models.

Total RNA derived from snap frozen tumor tissues of the 50 PDX models were prepared and purified using Tri® Reagent following standard protocol. Transcriptome sequencing was conducted on Illumina HiSeq 2500 platform, followed by RNAseq (as shown in Table 2) data analysis on the gene fusion with SOAPfuse and Defuse software.

TABLE 2

HNF4G-RSPO2 gene fusion was detected in PDX model GA3055

| Up_gene | PDX_model | Validation | UP_chr | Up_strand | Up_genome_pos | Dw_gene | Dw_chr |
|---|---|---|---|---|---|---|---|
| HNF4G | GA3055-P2 | Yes P6 | chr8 | + | 76402443 | RSPO2 | chr8 |
| HNF4G | GA3055-P3 | Yes P6 | chr8 | + | 76402443 | RSPO2 | chr8 |
| RSPO2 | GA3055-P3 | ND | chr8 | − | 109095035 | HNF4G | chr8 |

| Up_gene | Dw_strand | Dw_genome_pos | Spannum bysoapfuse | Juncnum bysoapfuse | Spannum bydefuse | Juncnum bydefuse |
|---|---|---|---|---|---|---|
| HNF4G | − | 109095035 | 5 | 15 | 8 | 19 |
| HNF4G | − | 109095035 | 10 | 15 | undetected | undetected |
| RSPO2 | + | 76402443 | undetected | undetected | 10 | 18 |

Gene expression data generated by RNA-seq technology from the 50 PDX gastric cancer models (see FIG. 3) was denoted using log 10(FPKM). The lowest log 10(FPKM) was set to −2. For genes whose log 10(FPKM) less than −2 were shown at −2 when the expression values were graphed. The genes and transcripts used for RNA-seq analysis were based on the ENSEMBL database version 66, it is convenient to search related gene information under the website of "http://feb2012.archive.ensembl.org/index.html".

A HNF4G-RSPO2 gene fusion was detected in a gastric cancer PDX model by transcriptome sequencing. This is the first report on such a gene fusion construct found in human gastric cancer xenograft samples.

In over 50 gastric PDX models examined, only one model was found to contain the HNF4G-RSPO2 gene fusion, which may represent a subpopulation of gastric cancer patients. The HNF4G-RSPO2 fusion event appears to activate the expression of the RSPO2 gene as the rest of the gastric cancer PDX models do not express the gene.

Example 2: Validation of the HNF4G-RSPO2 Gene Fusion in HuPrime® Cancer Tissue Models Using PCR In order to validate the presence of the fusion gene of HNF4G-RSPO2, RNA was extracted from HuPrime® cancer tissue models and purified using Tri® Reagent following standard protocol. The cDNA was then prepared using reverse transcription following standard protocol followed by gene-specific PCR amplification and direct sequence. The primers were designed as shown in Table 3 from the gene fusion junction location as shown in FIG. 4.

TABLE 3

Primer information

| Primer | SEQ ID NO: | Sequence | Amplicon Size |
|---|---|---|---|
| RSPO2/HNF4G-F | 7 | 5' CAGGAGCACCAGCGA AAG 3' | 323 bp |

TABLE 3-continued

Primer information

| Primer | SEQ ID NO: | Sequence | Amplicon Size |
|---|---|---|---|
| RSPO2/ HNF4G-R | 8 | 5' TGAGGGCAAAGGAGA AAAGG 3' | |

Figure 5:
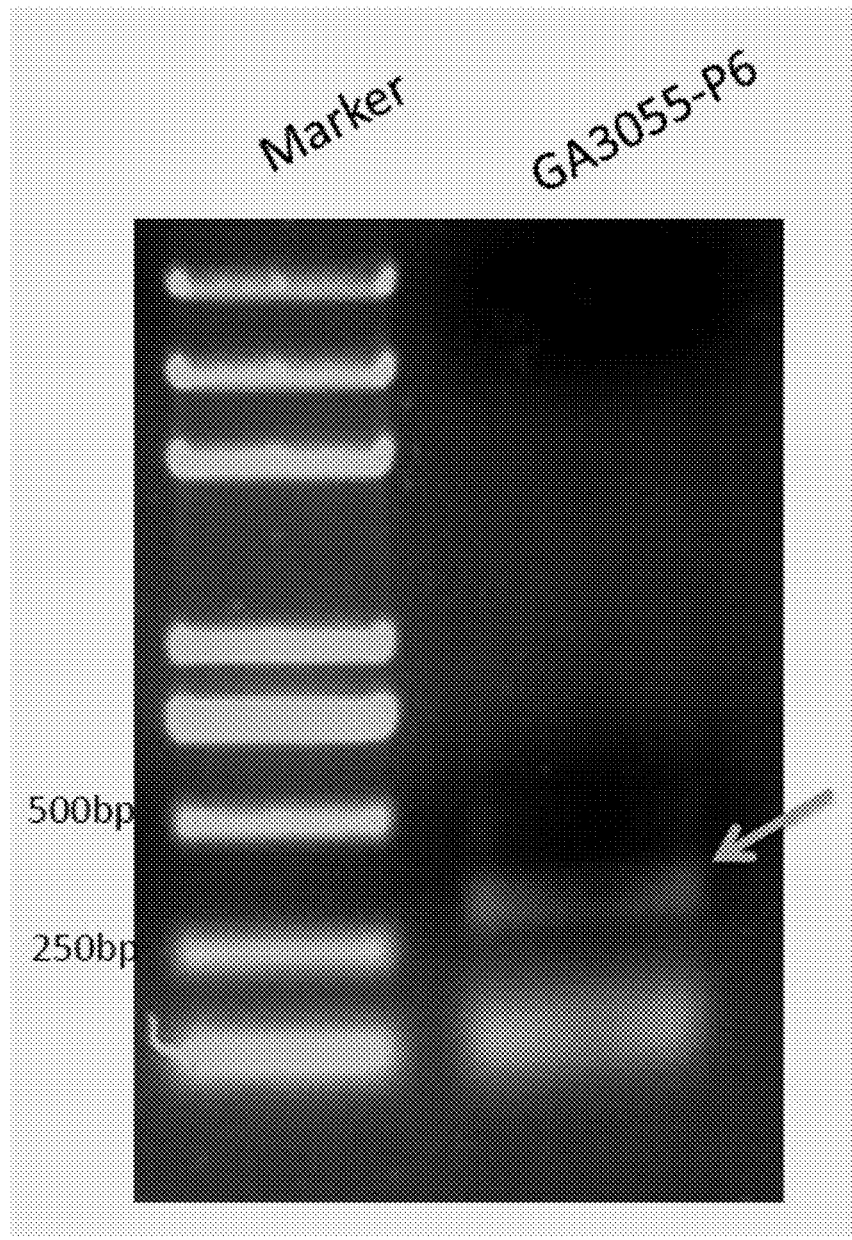
FIG. 5 indicates PCR amplification of the HNF4G-RSPO2 gene fusion junction region. The arrow points to the specific PCR product of expected size.

Polymerase chain reaction (PCR) was performed in 50 μl reactions composed of the following: 1 μl of sample cDNA, 5 μl of 10×PCR Buffer, 1 μl each of primers, 4 μl of dNTPs and 1 μl of TaqE. Cycling conditions were as follows: initial denaturation at 94° C. for 10 min followed by 40 cycles of denaturation at 94° C. for 30 s, annealing at 55-65° C. for 30 s and extension at 72° C. for 30 s, with a final extension at 72° C. for 7 min. The PCR product is visualized by agarose gel electrophoresis (see FIG. 5).

Figure 6:
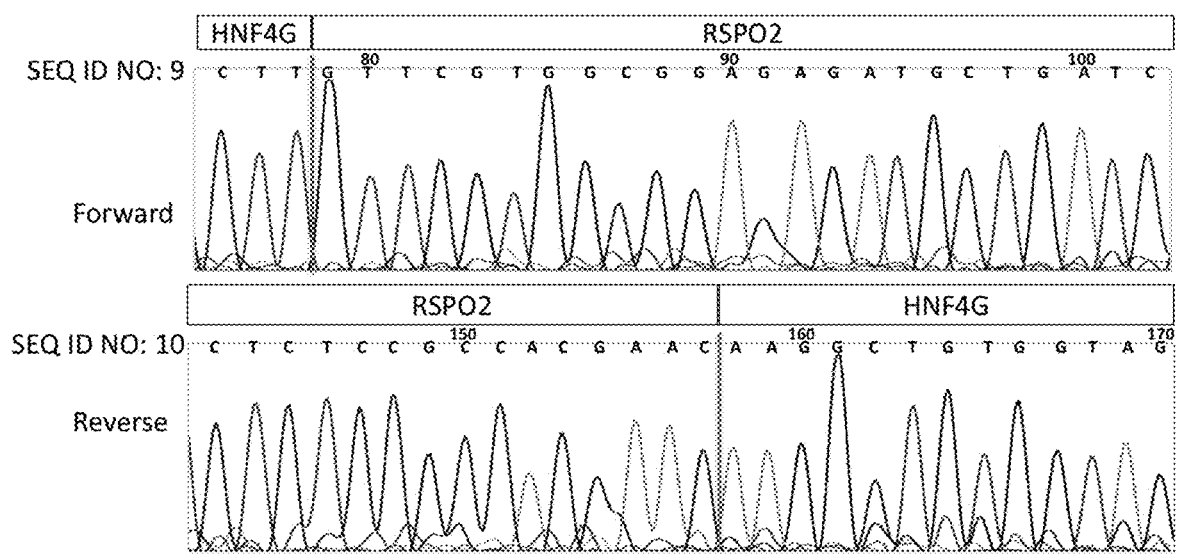
FIG. 6 shows the direct sequencing of RT-PCR product of the HNF4G-RSPO2 gene fusion junction region. The sequence of RT-PCR product for forward primer is SEQ ID NO:9 and the sequence of RT-PCR product for reverse primer is SEQ ID NO:10.

The PCR products were sequenced by Sanger sequencing method using forward (top) and reverse (bottom) primers, and the chromatograms are shown to have consistent sequence junction as detected by RNA sequencing (see FIG. 6). Therefore, the presence of HNF4G-RSPO2 gene fusion was confirmed by RT-PCR and direct sequencing.

Identification of the HNF4G-RSPO2 gene fusion in the gastric cancer PDX model provided a valuable tool for studying the tumorogenesis in cancer patients with similar genetic background. In addition, the gene fusion model also provided a valuable tool to evaluate novel anti cancer drugs that targets R-spondins or members in the Wnt signaling pathways.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method of detecting a fusion gene of HNF4G and RSPO2 in a nucleic acid-containing sample, comprising:
   a) contacting the sample with a detecting agent which specifically hybridizes to a fusion gene comprising a first encoding sequence for HNF4G and a second encoding sequence for RSPO2, and
   b) detecting the presence of the fusion gene,
      wherein the fusion gene comprises a fusion junction of CCACAGCCTT gttcgtggcg (SEQ ID NO: 3).

2. The method of claim 1, wherein the fusion gene is cDNA or snRNA.

3. The method of claim 1, wherein the detecting comprises contacting a first primer with the first encoding sequence for HNF4G, and contacting a second primer with the second encoding sequence for RSPO2.

4. The method of claim 1, wherein the detecting comprises contacting a junction primer with the fusion junction, and contacting a non-junction primer with the first or the second encoding sequence.

5. The method of claim 1, wherein the detecting comprises contacting a first probe with the first encoding sequence for HNF4G, and contacting a second probe with the second encoding sequence for RSPO2.

6. The method of claim 1, wherein the detecting comprises contacting a junction probe with the fusion junction.

7. The method of claim 1, further comprising detecting the amount of the fusion gene.

* * * * *

SEQUENCE LISTING

```
<160> NUMBER OF SEQ ID NOS: 10

<210> SEQ ID NO 1
<211> LENGTH: 143
<212> TYPE: DNA
<213> ORGANISM: Homo sapiens

<400> SEQUENCE: 1
agctccggga gcggcccgcg caggagcacc agcgaaagca gccagtctga gatattgaca      60
ctacagaaaa aactgacagc ttactccttg tattgattct actcttctct acaaatatag     120
actccgttcc ctaccacagc ctt                                             143

<210> SEQ ID NO 2
<211> LENGTH: 166
<212> TYPE: DNA
<213> ORGANISM: Homo sapiens

<400> SEQUENCE: 2
gttcgtggcg gagagatgct gatcgcgctg aactgaccgg tgcggcccgg gggtgagtgg      60
cgagtctccc tctgagtcct ccccagcagc gcggccggcg ccggctcttt gggcgaaccc     120
tccagttcct agactttgag aggcgtctct ccccccgcccg accgcc                   166

<210> SEQ ID NO 3
<211> LENGTH: 20
<212> TYPE: DNA
<213> ORGANISM: Homo sapiens

<400> SEQUENCE: 3
ccacagcctt gttcgtggcg                                                  20

<210> SEQ ID NO 4
<211> LENGTH: 331
<212> TYPE: DNA
<213> ORGANISM: Homo sapiens

<400> SEQUENCE: 4
gcggcccgcg cagtgattgc tgccttgacc gtccctgctc ttgaagagca ccagcgaaag      60
cagccagtct gagatattga cactacagaa aaaactgaca gcttactcct tgtattgatt     120
ctactcttct ctacaaatat agactccgtt ccctaccaca gccttgttcg tggcggagag     180
atgctgatcg cgctgaactg accggtgcgg cccgggggtg agtggcgagt ctccctctga     240
```

```
gtcctcccca gcagcgcggc cggcgccggc tctttgggcg aaccctccag ttcctagact      300
ttgagaggcg tctctccccc gcccgaccgc c                                    331

<210> SEQ ID NO 5
<211> LENGTH: 343
<212> TYPE: DNA
<213> ORGANISM: Homo sapiens

<400> SEQUENCE: 5
agctccggga gcggcccgcg caggagcacc agcgaaagca gccagtctga gatattgaca      60
ctacagaaaa aactgacagc ttactccttg tattgattct actcttctct acaaatatag     120
actccgttcc ctaccacagc cttgttcgtg gcggagagat gctgatcgcg ctgaactgac     180
cggtgcggcc cggggtgag tggcgagtct ccctctgagt cctccccagc agcgcggccg      240
gcgccggctc tttgggcgaa ccctccagtt cctagacttt gagaggcgtc tctccccgc      300 ccgaccgccc agatgcagtt tcgccttttc tcctttgccc tca                      343

<210> SEQ ID NO 6
<211> LENGTH: 165
<212> TYPE: DNA
<213> ORGANISM: Homo sapiens

<400> SEQUENCE: 6
gcggcccgcg cagtgattgc tgccttgacc gtccctgctc ttgaagagca ccagcgaaag      60
cagccagtct gagatattga cactacagaa aaaactgaca gcttactcct tgtattgatt     120
ctactcttct ctacaaatat agactccgtt ccctaccaca gcctt                     165

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7
caggagcacc agcgaaag                                                    18

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
tgagggcaaa ggagaaaagg                                                  20

<210> SEQ ID NO 9
<211> LENGTH: 27
<212> TYPE: DNA
<213> ORGANISM: Homo sapiens

<400> SEQUENCE: 9
cttgttcgtg gcggagagat gctgatc                                          27
```

```
<210> SEQ ID NO 10
<211> LENGTH: 28
<212> TYPE: DNA
<213> ORGANISM: Homo sapiens

<400> SEQUENCE: 10
ctctccgcca cgaacaaggc tgtggtag                                             28
```